(12) United States Patent
Lorraine et al.

(10) Patent No.: US 6,335,943 B1
(45) Date of Patent: Jan. 1, 2002

(54) SYSTEM AND METHOD FOR ULTRASONIC LASER TESTING USING A LASER SOURCE TO GENERATE ULTRASOUND HAVING A TUNABLE WAVELENGTH

(75) Inventors: Peter W. Lorraine, Niskayuna; Laurence Bigio, Schenectady; Robert J. Filkins, Fonda, all of NY (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 09/361,769

(22) Filed: Jul. 27, 1999

(51) Int. Cl.$^7$ ............................................... H01S 3/10
(52) U.S. Cl. ........................................................ 372/28
(58) Field of Search ............................... 372/26, 20, 28

(56) References Cited

U.S. PATENT DOCUMENTS

| 4,890,925 A | | 1/1990 | Kitamori et al. ............. 356/432 |
| 5,608,166 A | | 3/1997 | Monchalin et al. ............ 73/657 |
| 6,122,060 A | * | 9/2000 | Drake, Jr. .................... 356/359 |

FOREIGN PATENT DOCUMENTS

| EP | 0 757 242 A3 | 2/1997 | .......... G01N/21/17 |
| EP | 0 757 242 A2 | 2/1997 | .......... G01N/21/17 |

OTHER PUBLICATIONS

"Photoacoustic Waves Excited in Liquids by Fiber–Transmitted Laser Pulses", G. Paltauf and H. Schmidt–Kloiber, Institute of Experimental Physics, Karl Franzens–University Graz, Universitaetsplatz 5, A–8010 Graz, Austria.

"Real–Time Optical Characterization of Surface Acoustic Modes of Polyimide Thin–Film Coatings", Apr. R. Duggal, John A. Rogers, and Keith A. Nelson; Department of Chemistry, Massachusetts Institute of Technology, Cambridge, Massachusetts 02139.

* cited by examiner

Primary Examiner—Leon Scott, Jr.
(74) Attorney, Agent, or Firm—Hughes & Luce, LLP

(57) ABSTRACT

A system and method for generating ultrasonic displacements on a remote target. The method of the present invention includes the steps of first using a laser to generate a beam having a first wavelength to produce ultrasonic displacements at the remote target. This laser beam will have a first wavelength which can be modulated to alter characteristics of the ultrasonic displacements. These ultrasonic displacements at the remote target can be optimized to enhance the detection optics for collecting phase modulated light from the second pulsed laser beam either reflected or scattered by the remote target; an interferometer to process the phase modulated light and generate at least one output signal, and means for processing the at least one output signal to obtain data representative of the ultrasonic surface displacements on the surface of the remote target.

53 Claims, 3 Drawing Sheets

SYSTEM AND METHOD FOR ULTRASONIC LASER TESTING USING A LASER SOURCE TO GENERATE ULTRASOUND HAVING A TUNABLE WAVELENGTH

TECHNICAL FIELD OF THE INVENTION

This invention relates generally to the field of optical information processing and more particularly to a method and apparatus for ultrasonic laser testing. More specifically, the present invention provides an improved laser source for generation of ultrasound. Even more particularly, the laser source of the present invention can significantly improve the characteristics of the ultrasound generated by modulating the optical and temporal characteristics of the generation laser to optimize the characteristics of the generated ultrasound.

BACKGROUND OF THE INVENTION

In recent years, the use of advanced composite structures has experienced tremendous growth in the aerospace, automotive, and many other commercial industries. While composite materials offer significant improvements in performance, they require strict quality control procedures in the manufacturing processes. Specifically, non-destructive evaluation ("NDE") methods are required to assess the structural integrity of composite structures, for example, to detect inclusions, delaminations and porosities. Conventional NDE methods are very slow, labor-intensive, and costly. As a result, testing procedures adversely increase the manufacturing costs associated with composite structures. Various methods and apparatuses have been proposed to assess the structural integrity of composite structures. One method to discloses the use of a pulsed laser beam for generating ultrasound on a work piece and a second pulsed laser beam for detecting the ultrasound. Phase modulated light from the second laser beam is then demodulated to obtain a signal representative of the ultrasonic motion at the surface of the work piece. A disadvantage associated with this approach is that the first pulsed laser beam is not optimized for the generation of ultrasound in the workplace.

Prior solutions describe operable techniques for optically detecting transient motion from a scattering surface, which techniques are useful for ultrasonic composite materials non-destructive test and evaluation, these techniques have numerous failings.

Known techniques provide the ability to perform common mode noise cancellation. By using a single laser signal, the known techniques cannot perform differential mode operation. An adverse consequence of this characteristic is the inability to use known ultrasonic systems in factory or industrial settings where ambient light noise levels exceed certain threshold levels. This problem prevents the proper detection of scatter signals from the composite materials.

Another limitation associated with none ultrasonic test and evaluation techniques relates to their broad scanning approaches to determine the existence of a transient, thereby indicating a defect. Because broad scanning occurs, both the amount of data is excessive and the degree of accuracy is lower.

Another limitation associated with the known systems relates to their ability to process ultrasonic data in real-time. This limitation makes such systems only marginally useful for testing and evaluating composite materials.

Other limitations associated with existing systems relate to general inflexibility of such systems, which may hold all distances low, result in small depth of field performance and only minimal extraction of information from the back scattered signals. These limitations make industrial application of the ultrasonic testing method generally impractical.

Therefore, it would be desirable for a new method and apparatus for ultrasonic laser testing that overcomes the disadvantages and deficiencies of the prior art.

SUMMARY OF THE INVENTION

In light of the above, a need exists for a system and method that generates a desired frequency content in laser-generated ultrasonic waves. The present invention provides a system and method for generating laser radiation with a tunable wavelength and temporal shape that substantially eliminates or reduces disadvantages and problems associated with previously developed systems and methods for laser inspection.

More specifically, the present invention provides a system for generating laser radiation with a tunable wavelength and temporal shape. This system includes a first pulsed laser to generate a first pulse laser beam. The first pulse laser beam is produced having a first wavelength. A wavelength shifting device shifts the first wavelength of the first laser beam to a second wavelength. A modulator then modulates the laser beam having the second wavelength.

In another embodiment, the laser radiation with a tunable wavelength is utilized to generate ultrasonic displacements at a remote target to be inspected. This involves generating a first laser beam having a first wavelength. A wavelength shifting device then shifts the first wavelength of the first laser beam to a second wavelength. An optical modulator is used to modulate the second wavelength laser beam's temporal shape. This laser beam is then used to generate ultrasonic displacements at a remote target wherein the ultrasonic displacements at the remote target have a desired frequency content and are used for NDE of the remote target.

The present invention provides an important technical advantage in that a laser-generated ultrasonic wave can be formed with a desired frequency content and temporal shape. Thus, for certain materials that require specific ranges of acoustic frequency to adequately perform a non-destructive evaluation of the material, an optimal set of ultrasonic displacements can be determined. In turn, the wavelength shifting device is used to shift the first wavelength to a wavelength, which generates the optimal laser pulse to produce the desired range of acoustic energy in the ultrasonic wave. Therefore, depending on the thickness or composition of the materials, the desired ultrasonic displacements can be generated to produce the best resolution for inspection.

Additionally, the attenuation of the ultrasound can be controlled, allowing a user to optimize the inspection techniques for the defects to be searched for. Furthermore, by understanding the attenuation characteristics of the ultrasound generated in the target, the scanning technique can be optimized based on these characteristics to reduce or eliminate over sampling and therefore increase the speed and efficiency of the inspection which decreasing cost.

The present invention provides another technical advantage in that a system is provided for flexible, accurate, and cost-effective methods for inspecting complex composite structures. The present invention is able to optimize a scan and test a large size composite structure based on empirical data associated with the composite structure or data modeled on the composition of the structure.

BRIEF DESCRIPTION OF THE DRAWINGS

A more complete understanding of the present invention and the advantages thereof may be acquired by referring to the following description, taken in conjunction with the accompanying drawings in which like reference numbers indicate like features and wherein.

DETAILED DESCRIPTION OF THE INVENTION

Preferred embodiments of the present invention are illustrated in the FIGUREs, like numerals being used to refer to like and corresponding parts of various drawings.

The present invention provides a system and method for generating laser radiation with a tunable wavelength and temporal shape that substantially eliminates or reduces disadvantages and problems associated with previously developed systems and methods for laser inspection.

More specifically, the present invention provides a system for generating laser radiation with a tunable wavelength and temporal shape. This system includes a first pulsed laser to generate a first pulse laser beam. The first pulse laser beam is produced having a first wavelength. A wavelength shifting device shifts the first wavelength of the first laser beam to a second wavelength. A modulator then modulates the laser beam having the second wavelength.

Figure 1:
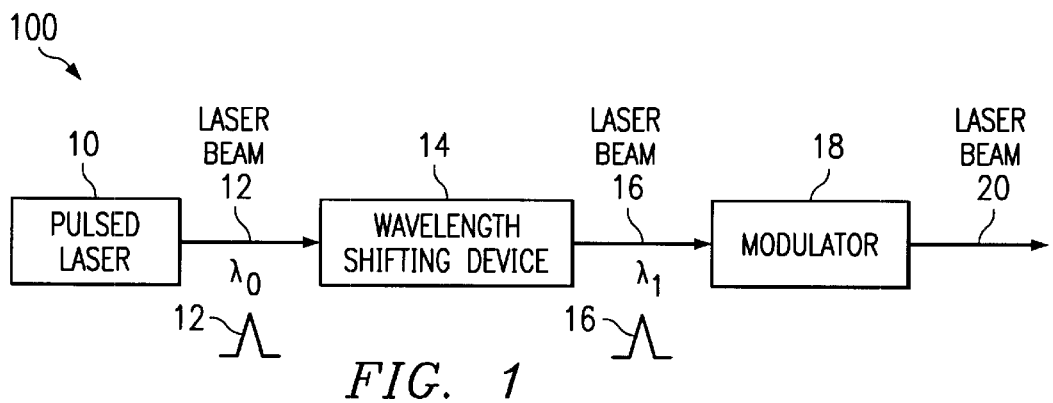
FIG. 1 provides a first embodiment of the present invention.

FIG. 1 shows in a block diagram the basic components of system 100 for generating laser radiation with a tunable wavelength and temporal shape. System 100 comprises a pulsed laser 10 which will generate a laser beam 12 having a first wavelength $\lambda 0$. The first laser beam 12 will have a path of propagation to a wavelength shifting device 14. This wavelength shifting device will shift the first wavelength $\lambda 0$ to a second wavelength $\lambda 1$, producing a laser beam 16 having a second wavelength $\lambda 1$. Laser beam 16 may then be modulated by an optical modulator 18 to produce a laser beam 20 having a tunable temporal shape. In the present invention, wavelength shifting device 14 may be an optical parametric oscillator, RAMAN cell, difference frequency generators, or a device combining a second laser beam with the first to generate a laser having wavelength $\lambda 1$.

Pulsed laser 10 may be a CO2 laser, neodymium YAG laser (Nd:Yag laser), alexandrite laser, titanium sapphire laser, diode pumped laser, lamp pumped laser, or other laser known by those skilled in the art. The second wavelength chosen may be chosen in order to be compatible with an optical carrier used to transmit the laser to a remote target, or may be selected to an optical wavelength $\lambda 1$.

In one embodiment of the present invention, a second wavelength may be chosen in order to optimize characteristics of the interaction of the laser beam with a target material, such as in the generation of ultrasound in a material for NDE inspection. For example, a laser-generated ultrasonic wave can be generated by the laser with a desired frequency content and penetration depth, and wherein the ultrasonic displacements have a desired frequency content. Therefore, depending on the thickness of the material or material composition to be tested, the desired frequencies and ultrasonic displacements can be generated to produce the best resolution for the specific NDE inspection at hand. This second wavelength may be an optimal wavelength that is determined from either material-specific data or empirically calculated data associated with the material to be tested. This data may vary for different materials and thicknesses of these materials. A specific embodiment of the present invention uses a diode pumped laser with an OPO for operation at 3.5 microns. In another example, the first wavelength may be 1064 nm and the second wavelength may be 3500 nm, or the second wavelength may be chosen between 1000 nm and 4000 nm.

The first laser may be transmitted to the wavelength shifting device by an optical fiber mechanism. This optical fiber mechanism may deliver CO2 laser radiation operating at 10 microns. After the wavelength of laser 12 has been shifted from a first wavelength $\lambda 0$ to a second wavelength $\lambda 1$, a modulator 18 may be used to encode a long-source laser pulse such as a tone burst, chirp, more complex modulation schemes to control the generated ultrasonic displacements spectral or content, or provide a basis for match filter detection.

Figure 2:
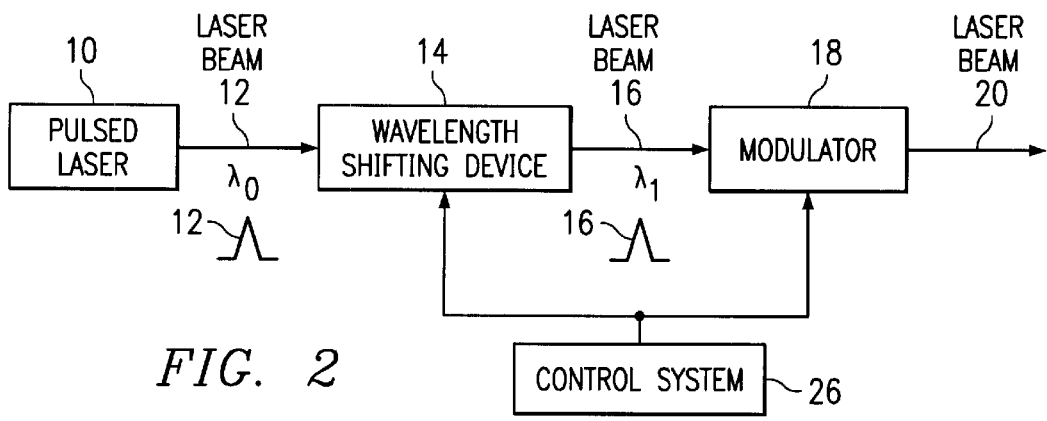
FIG. 2 illustrates an embodiment of the present invention utilizing a control system.

FIG. 2 shows an additional embodiment of the present invention wherein a computer control system 22 is coupled to the wavelength shifting device 14 and modulator 18. This control system 22 may be utilized to dynamically control the wavelength shifting device 14 and modulator 18 such that an optimal second wavelength $\lambda 1$ and the temporal shape of the laser 20 can be dynamically altered during an inspection to optimize an NDE test.

Figure 3:
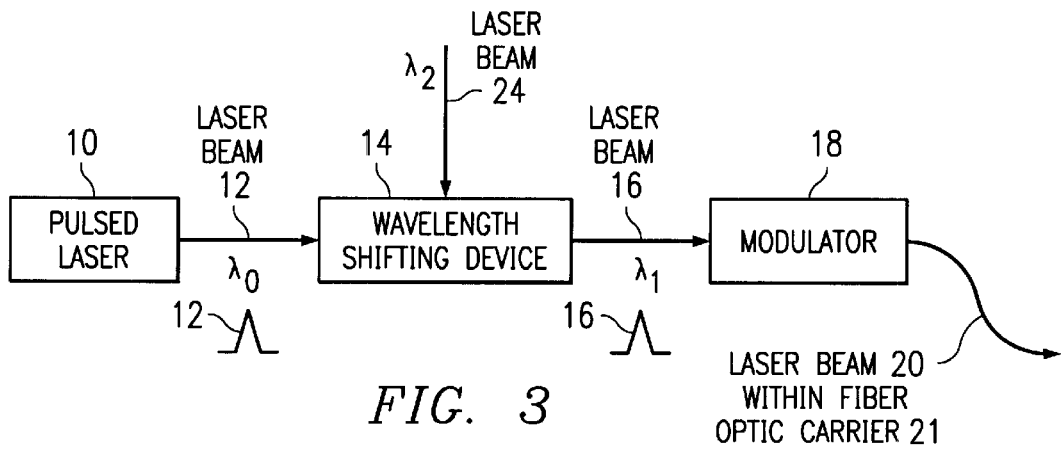
FIG. 3 illustrates a second embodiment of the present invention wherein wavelength shifting is accomplished using a second laser.

FIG. 3 is similar to FIG. 1. However, the wavelength shifting device may combine a second laser 24 with first laser 12 to produce a new laser beam 16 having a second wavelength $\lambda 1$.

FIG. 4 again is similar to FIG. 1, however FIG. 4 incorporates a filter to filter laser beam 12 prior to shifting the wavelength of laser beam 12 to $\lambda 1$ in order to improve a signal-to-noise ratio of the first laser beam.

A specific embodiment of the present invention may utilize a solid-state laser such as a Nd:YAG laser. The optical wavelength may be shifted to match the optical attenuation properties of the material under test. A preferred embodiment produces laser pulses between 2.5 and 4 microns in optical wavelength and even more specifically between 3.5 and 3.8 microns in optical wavelength.

In the present invention, an optical fiber of silver chloride/silver bromide (Ag:Br) glass may be used to deliver a laser pulse. More specifically, this optical fiber may be used to deliver a 10 micron CO2 laser pulse, or other far IR laser pulse for ultrasonic purposes. This optical fiber has more far IR applications than previous materials such as ZBLAN.

Figure 5:
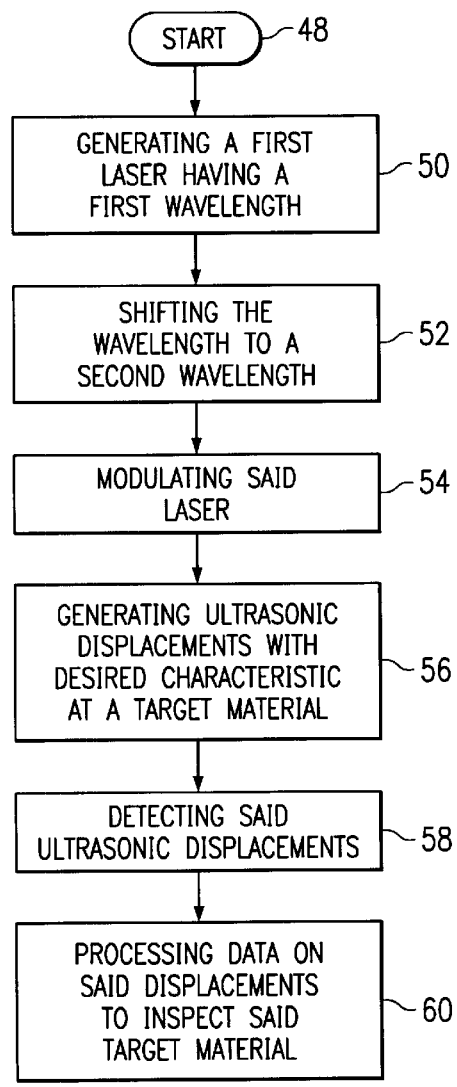
FIG. 5 provides a flow chart of the present invention.

FIG. 5 presents a method of the present invention wherein laser radiation having a tunable wavelength and temporal shape is used to generate ultrasonic displacements at a remote target for NDE. At step 50, a first laser have a first wavelength is generated.

At step 52, this first laser is shifted in wavelength to a second wavelength. This second wavelength may be chosen in order to generate desirable characteristics in the ultrasonic displacements. This shifting the wavelength of the first laser may be accomplished using an optical parametric oscillator, combining the first laser with a second laser to produce a laser beam having a second wavelength, or other method as known to those skilled in the art. At step 54, the laser beam having the second wavelength may be modulated to alter the temporal shape or frequency content of the laser. This modulated laser may then be applied to a remote target in or to generate ultrasonic displacements. This is accomplished in step 56.

The ultrasonic displacements generated at the target may be detected to determine flaws, porosities, or other defects (as known by those skilled in the art) in a remote target. One such method may involve using a pulsed laser beam applied coaxially with the ultrasound generating laser to detect the ultrasonic displacements at the remote target. The ultrasonic displacements at the remote target will create phase-modulated light that is scattered and reflected from the coaxially applied laser. This phase-modulated light may be processed in order to obtain data representative of the ultrasonic displacements at the remote target. The data associated with the ultrasonic displacements may be processed to discover flaws, defects, or other porosities in the material under test of the remote target. These functions are represented by step 58 which involves detecting the ultrasonic displacements at a remote target, and step 60 processing the data associated with the ultrasonic displacements in order to perform a non-destructive evaluation of the remote target.

Figure 4:
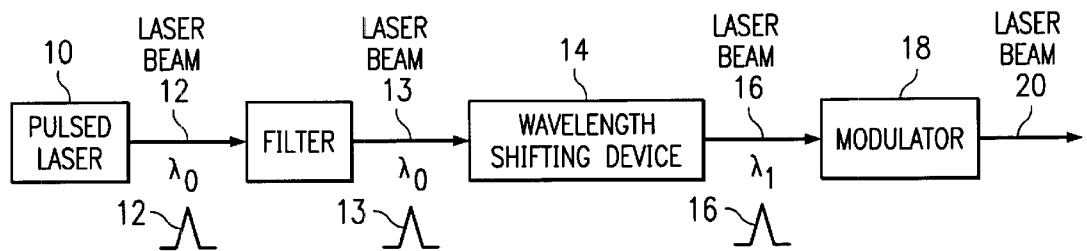
FIG. 4 provides a process to reduce noise associated with the generation laser of the present invention.
Figure 6:
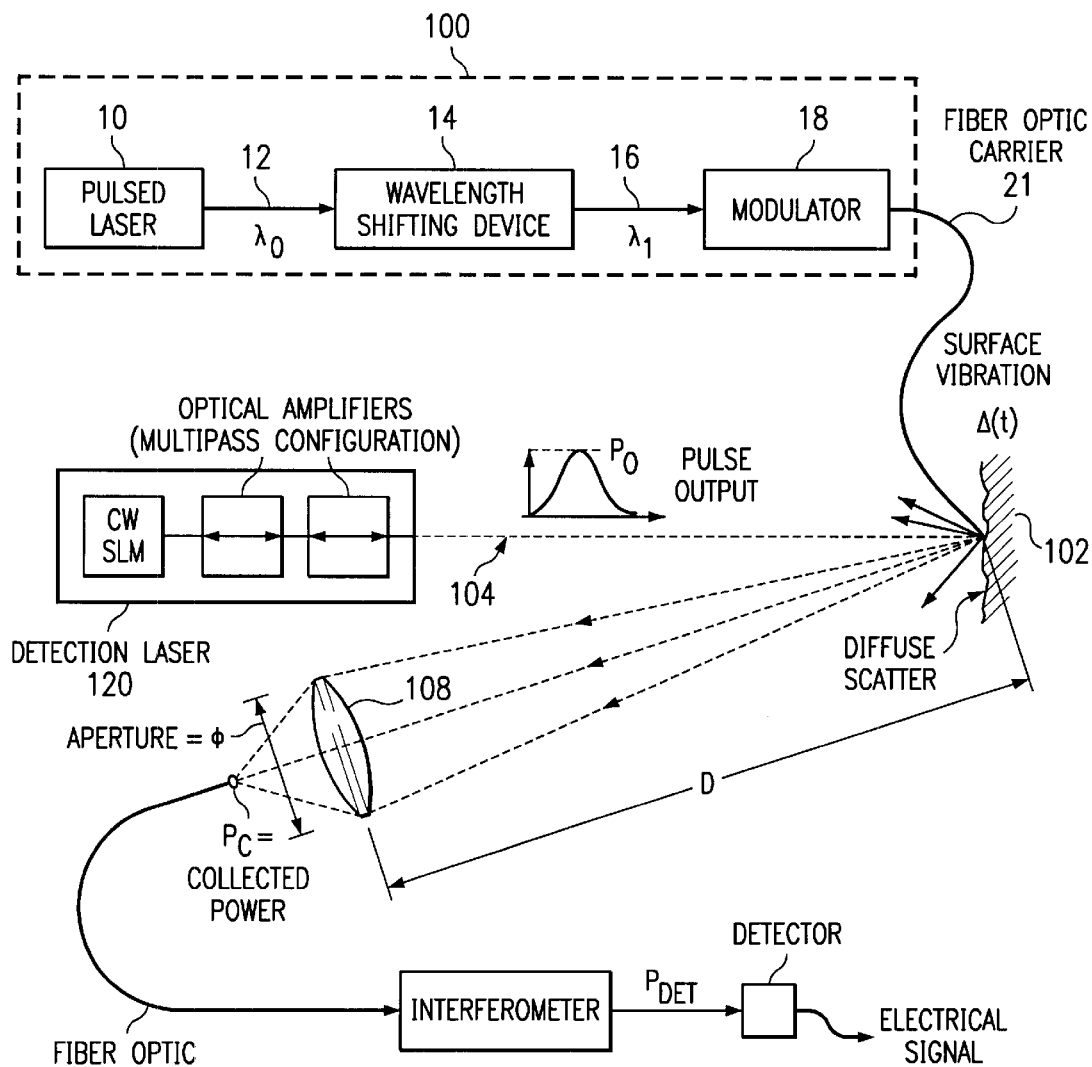
FIG. 6 provides a block diagram of the present invention wherein the present invention is utilized in conjunction with a laser detection system for detecting ultrasonic displacements.

FIG. 6 describes a system for generating ultrasonic displacements at a remote target utilizing a laser with tunable wavelength in temporal shape. System 100, or other embodiments of the present invention as illustrated in FIGS. 2, 3 and 4, may be utilized to generate a laser having tunable wavelength and temporal shape. This laser may be applied by a fiber optic carrier 21 to a remote target 102. A material such as ZBLAN, or Ag:Br glass may be selected for optical carrier 20. A long pulse may be encoded into laser 20 by encoding the long pulse prior to shifting from a first wavelength of laser 12 to a second wavelength of laser 16. This long pulse may be dynamically controlled by a computer system 26 in order to alter an inspection acoustic frequency or a depth of inspection. These encoded pulses may include a tome burst or chirp to control the inspection acoustic frequency. The need to dynamically control this long pulse might arise from different polymers in a composite or different thicknesses in different regions of remote target 102.

A detection laser 104 may be applied to the remote target 102. In one embodiment (not shown), this detection laser 104 may be applied coaxially with generation laser 20. Generation laser 20 produces a compressional ultrasonic displacement in the material of target 102. The ultrasonic displacement is a result of thermo-elastic expansion of the material of target 102 as it absorbs generation laser 20. Generation laser 20 must be of a frequency that is readily absorbed at the desired depth in remote target 102 without causing ablation or damage to the material of target 102. Furthermore, generation laser 20 must be of a long enough pulse to induce ultrasonic deformations. Generation laser 20 should be absorbed into remote target 102 as heat, thereby causing thermo-elastic expansion without ablation. Generally, utilizing a wavelength in the ultraviolet range is undesirable because such light can potentially damage a composite material if remote target 102 is made of such. Detection laser 104 must be of a frequency that does not induce further ultrasonic displacements at remote target 102.

Detection laser 104 interacts with ultrasonic displacements at remote target 102 and produces phase-modulated light 106. Some of the phase-modulated light 106 may be captured by collection optics 108. Methods for detecting such ultrasonic displacements are disclosed in U.S. patent application Ser. No. 09/345,558, entitled "Method and Apparatus For Detecting Ultrasonic Surface Displacements Using Post-Collection Optical Implementation," filed on Jun. 30, 1999, to Thomas E. Drake, and U.S. patent application Ser. No. 09/343,920, entitled "Method and Apparatus For Ultrasonic Laser Testing," filed on Jun. 30, 1999, to Thomas E. Drake. These patent applications are hereby incorporated by reference.

The embodiments disclosed in the present invention may be combined with the techniques described in the above U.S. Patent Applications and U.S. patent application Ser. No. 09/361,768, entitled "System and Method For Laser-Ultrasonic Frequency Control Using Optical Wavelength Tuning," filed on Jul. 27, 1999, to Marc Dubois, et. al., which is incorporated by reference, to provide control of the acoustic frequency content by either optical wavelength control or temporal modulation. A further extension is a combination of optical wavelength shifting, spatial modulation, or patterning of the laser source.

The present invention provides an important technical advantage in that a laser-generated ultrasonic wave can be generated with a desired frequency content and temporal shape. Thus, for certain materials and geometries that require specific frequency range or temporal shape to adequately inspect the material, optimal ultrasonic displacements may be generated by a laser having optimal optical characteristics. An optimal wavelength $\lambda 1$ for generation laser 20 may be determined. Then generation laser 20 may be used to generate the desired ultrasonic displacements at a remote target to be inspected. Hence, the desired ultrasonic displacements can be generated and in turn produce increased resolution for target inspection. Additionally, inspection scanning of a remote target can be optimized based on the attenuation characteristics of the ultrasonic displacements generated at the remote target. Although this enhances and optimizes the efficiency of the non-destructive evaluation testing of materials, this reduces costs and inspection time associated with these materials.

Although the present invention has been described in detail herein with reference to the illustrative embodiments, it should be understood that the description is by way of example only and is not to be construed in a limiting sense. It is to be further understood, therefore, that numerous changes in the details of the embodiments of this invention and additional embodiments of this invention will be apparent to, and may be made by, persons of ordinary skill in the art having reference to this description. It is contemplated that all such changes and additional embodiments are within the spirit and true scope of this invention as claimed below.

What is claimed is:

1. A method for controllably generating ultrasonic displacements at a remote target, comprising the steps of:

generating a laser beam of pulses at a first known wavelength;

directing the laser beam to a point on the remote target for producing ultrasonic displacement on the remote target;

sensing ultrasonic displacements at the remote target;

tuning the first known wavelength of said laser beam to a second wavelength in the 3- to 4-micron range for altering the ultrasonic displacements occurring at the remote target in response to said laser beam, said tuning for generating optimal resolution of said ultrasonic displacements during said sensing.

2. The method of claim 1, further comprising the step of modulating the amplitude of the laser beam to generate optimal resolution of said ultrasonic displacements during said sensing.

3. The method of claim 1, wherein the step of tuning the first known wavelength of the laser beam to a second wavelength is realized with an optical parametric oscillator.

4. The method of claim 1, wherein the first known wavelength is 1064 nm and the second wavelength is 3500 nm.

5. The method of claim 1, wherein the second wavelength is in the rage of 1000 to 4000 nm.

6. The method of claim 1, wherein the second wavelength is compatible with a flexible optical conduit.

7. The method of claim 6, wherein the flexible optical conduit is a fiber optic carrier.

8. The method of claim 7, further comprising reducing the peak power of the first laser by temporally controlling the pulse width.

9. The method of claim 6, wherein the fiber optic carrier is constructed from material selected from the group consisting of Zblan and silver chloride/silver bromide glass.

10. The method of claim 1 further comprising the step of encoding a long source laser pulse prior to tuning the first known wavelength of the laser beam to a second wavelength.

11. The method of claim 10, wherein the step of encoding a long pulse laser source is dynamically controlled by a computer system to alter set of variables comprising:
an inspection acoustic frequency; and
a depth of penetration.

12. The method of claim 11, wherein the long pulse laser source is encoded with a tone burst to control the inspection acoustic frequency.

13. The method of claim 11, wherein the long pulse laser source is encoded with a chirp to control the inspection acoustic frequency.

14. The method of claim 11, wherein the long pulse laser source is varied based on a specific composite formulation of the remote target.

15. The method of claim 11, wherein the long pulse laser source is varied based on a geometry of the remote target.

16. The method of claim 11, wherein the long pulse laser source is varied based on a database used to determine the optimal inspection acoustic frequency and depth of penetration.

17. The method of claim 1, wherein the first laser has a repetition rate greater than 400 Hz.

18. The method of claim 1, wherein the first laser is selected from the group consisting of CO2 Laser, Nd:YAG laser, alexandrite laser, titanium sapphire laser, lamp pumped laser, and diode pumped laser.

19. The method of claim 1, wherein the first laser is a solid state laser.

20. The method of claim 1, wherein the long pulse laser source is controllably varied based on a specific composite formulation of the remote target.

21. The method of claim 1, wherein the step of tuning the first known wavelength of the laser beam to a second wavelength is realized by combining the first laser with a second laser to produce a third laser at a second wavelength.

22. A method for controllably producing laser radiation with a tunable wavelength and temporal shape comprising:
generating a laser beam of pulses having a first known wavelength;
directing said laser beam to a point on the remote target for producing ultrasonic displacements on the remote target;
sensing the ultrasonic displacements on the remote target;
tuning the first known wavelength of said laser beam to a second wavelength in the 3- to 4-micron range for altering the ultrasonic displacement occurring at the remote target in response to said laser beam, said controllable shifting for generating optimal resolution of said ultrasonic displacements during said sensing.

23. The method of claim 22, wherein the step of tuning the first known wavelength of the laser beam to a second wavelength is realized with an optical parametric oscillator.

24. The method of claim 22, wherein the first wavelength is 1064 nm and the second wavelength is 3500 nm.

25. The method of claim 22, wherein the second wavelength is 1000 to 4000 nm.

26. The method of claim 22, wherein the second wavelength is compatible with a flexible optical conduit.

27. The method of claim 26, wherein the flexible optical conduit is a fiber optic carrier.

28. The method of claim 27, wherein the fiber optic carrier is constructed from Zblan.

29. The method of claim 27, wherein the fiber optic carrier is constructed from silver chloride/silver bromide glass.

30. The method of claim 27, further comprising reducing the peak power of the first laser by temporally controlling the pulse width.

31. The method of claim 23, further comprising the step of encoding a long source laser pulse prior to tuning the first wavelength of the first laser beam to a second wavelength.

32. The method of claim 31, wherein the step of encoding a long pulse laser source is dynamically controlled by a computer system.

33. The method of claim 32, wherein the long pulse laser source is encoded with a tone burst.

34. The method of claim 32, wherein the long pulse laser source is encoded with a chirp.

35. The method of claim 32, wherein the first laser has a repetition rate greater than 400 Hz.

36. The method of claim 22, wherein the first laser is selected from the group consisting of CO2 Laser, Nd:YAG laser, alexandrite laser, titanium sapphire laser, lamp pumped laser, and diode pumped laser.

37. The method of claim 22, wherein the first laser is a solid state laser.

38. The method of claim 22, wherein the step of tuning the first wavelength of the first laser beam to a second wavelength is realized by combining the first laser with a second laser to produce a new laser beam at a second wavelength.

39. The method of claim 22, further comprising the step of filtering the first laser beam prior to tuning the wavelength of the laser beam to improve a signal to noise ratio of the first laser beam.

40. A system for producing laser radiation with a tunable wavelength and temporal shape comprising:
a laser for generating a pulsed laser beam having a first known wavelength;
a laser beam directing mechanism for directing said laser beam to a point on the remote target;
an ultrasonic displacement sensor for sensing ultrasonic displacements at the remote target;
a wavelength shifting device for tuning the first known wavelength to a second wavelength in the 3- to 4-micron range for generating optimal resolution of said ultrasonic displacements for said ultrasonic displacement sensor.

41. The system of claim 40, wherein the wavelength shifting device is an optical parametric oscillator.

42. The system of claim 40, wherein the first wavelength is 1064 nm and the second wavelength is 3500 nm.

43. The system of claim 40, wherein the second wavelength is 1000 to 4000 nm.

44. The system of claim 40, wherein the second wavelength is compatible with a flexible optical conduit.

45. The system of claim 44, wherein the flexible optical conduit is a fiber optic carrier.

46. The system of claim 40, further comprising an encoder to encode a long source laser pulse prior to tuning the first wavelength of the first laser beam to the second wavelength.

47. The system of claim 46, further comprising a computer system to dynamically control the encoding a long pulse laser source.

48. The system of claim 40, wherein the first laser is selected from the group consisting of CO2 Laser, Nd:YAG laser, alexandrite laser, titanium sapphire laser, pumped diode and lamped pumped laser.

49. The system of claim 40, wherein the first laser is a solid state laser.

50. The system of claim 40, further comprising a fiber optic carrier constructed from Zblan to coupled to the first pulsed laser to deliver the first laser to a point on a remote target.

51. The system of claim 50, wherein a peak power of the first laser is reduced by temporally controlling the pulse width.

52. The system of claim 40, wherein the wavelength shifting device combines the first laser with a second laser to produce a new laser beam at a second wavelength.

53. The system of claim 40, further comprising an optical filter to filter the first laser beam prior to tuning the wavelength of the laser beam to improve a signal to noise ratio of the first laser beam.

* * * * *